US012440616B2

(12) United States Patent
Stefan et al.

(10) Patent No.: US 12,440,616 B2
(45) Date of Patent: Oct. 14, 2025

(54) TRAY FOR RECEIVING A PLURALITY OF MEDICAL HOLLOW BODIES

(71) Applicant: Vetter Pharma-Fertigung GmbH & Co. KG, Ravensburg (DE)

(72) Inventors: Ralph Stefan, Ebenweiler (DE); Markus Behrendt, Berg (DE); Holger Pupke, Balingen (DE); Karoline Moller, Ravensburg (DE)

(73) Assignee: Vetter Pharma-Fertigung GmbH & Co. KG, Ravensburg (DE)

( * ) Notice: Subject to any disclaimer, the term of this patent is extended or adjusted under 35 U.S.C. 154(b) by 0 days.

(21) Appl. No.: 18/010,929

(22) PCT Filed: Jun. 11, 2021

(86) PCT No.: PCT/EP2021/065868

§ 371 (c)(1),
(2) Date: Dec. 16, 2022

(87) PCT Pub. No.: WO2021/254918

PCT Pub. Date: Dec. 23, 2021

(65) Prior Publication Data

US 2024/0226419 A1 Jul. 11, 2024

(30) Foreign Application Priority Data

Jun. 18, 2020 (DE) ..................... 10 2020 207 588.3

(51) Int. Cl.
*A61M 5/00* (2006.01)
*B65D 1/36* (2006.01)
*B65D 25/10* (2006.01)

(52) U.S. Cl.
CPC ............... *A61M 5/008* (2013.01); *B65D 1/36* (2013.01); *B65D 25/103* (2013.01)

(58) Field of Classification Search
CPC .......... B65D 25/103; B65D 1/36; B65D 1/34; B65D 25/10; A61M 5/002; A61M 5/008; A61M 5/3202
(Continued)

(56) References Cited

U.S. PATENT DOCUMENTS 4,753,345 A * 6/1988 Goodsir ............... B65D 25/105 206/365
5,339,955 A * 8/1994 Horan .................... A61B 50/33 206/370
(Continued)

FOREIGN PATENT DOCUMENTS

DE 1919964 U 7/1965
DE 69629281 T2 5/2004
(Continued)

OTHER PUBLICATIONS

International Search Report and Written Opinion for PCT/EP2021/065868 dated Sep. 14, 2021, 18 pages. English translation of ISR only.
(Continued)

*Primary Examiner* — Steven A. Reynolds
(74) *Attorney, Agent, or Firm* — Sheppard Mullin Richter & Hampton LLP

(57) ABSTRACT

The invention relates Tray (1) for holding a plurality of medical hollow bodies (49), comprising
a bottom plate (3) having a top side (5) and a bottom side (7), wherein
an all-around wall (11) is disposed along outer edges (9) of the tray (1) on the top side (5), wherein
the bottom plate (3) and the wall (11) delimit a receiving volume (13) for receiving the medical hollow bodies (49), wherein
(Continued)

Figure 1:
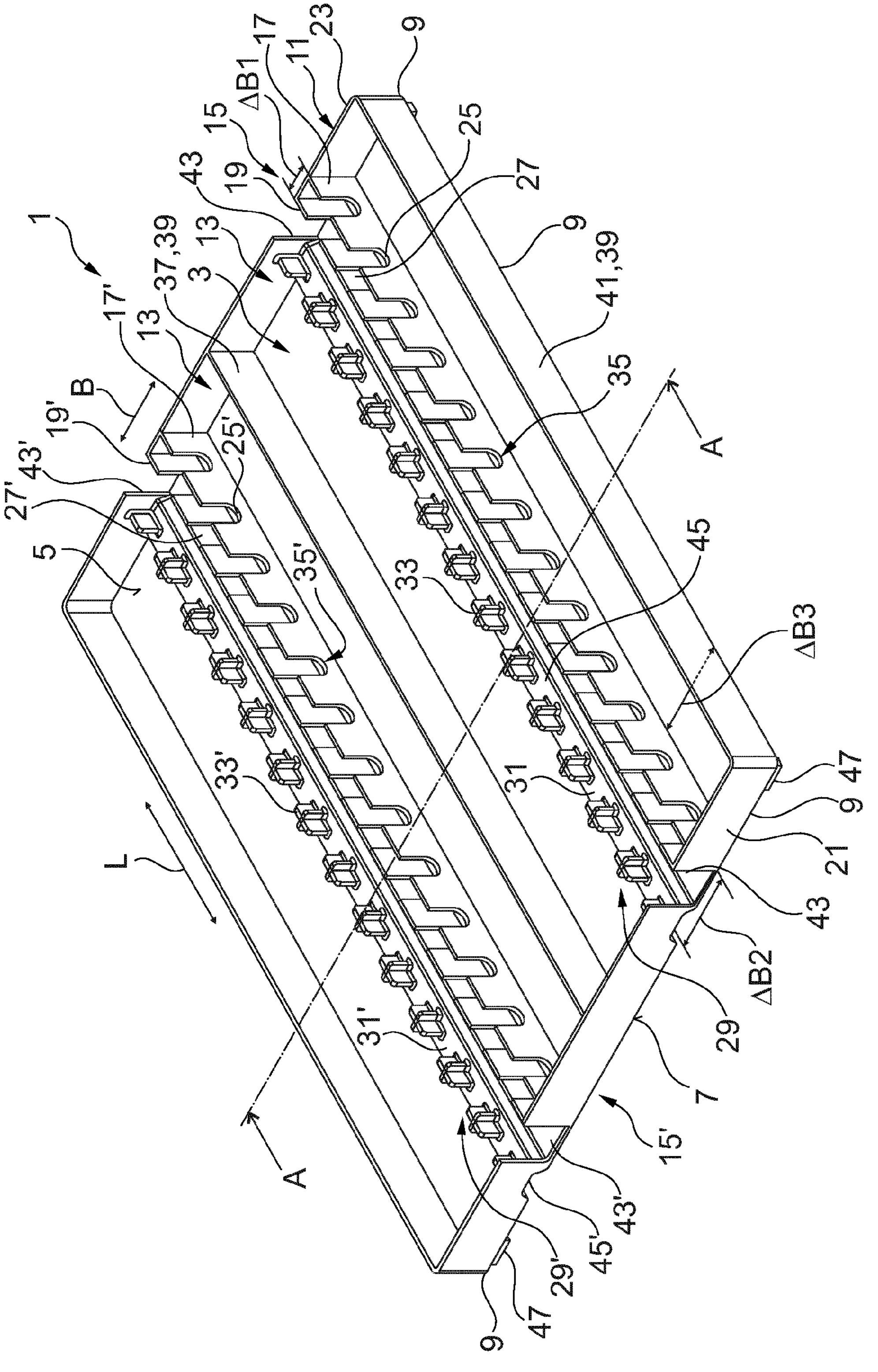

the tray (1) has a finite length along a longitudinal direction (L) and a finite width along a width direction (B) perpendicular to the longitudinal direction (L), wherein the tray (1) comprises at least one holding structure (15) for holding medical hollow bodies (49), wherein the at least one holding structure (15) comprises a first holding wall (17), a second holding wall (19) and a row of distance elements (33).

10 Claims, 3 Drawing Sheets

(58) Field of Classification Search
USPC .................................. 206/438, 571, 364, 366
See application file for complete search history.

(56) References Cited

U.S. PATENT DOCUMENTS

| | | | | |
|---|---|---|---|---|
| 5,772,031 | A * | 6/1998 | Landis | A61B 50/30 206/363 |
| 6,216,885 | B1 * | 4/2001 | Guillaume | B65D 71/70 206/564 |
| 9,216,253 | B2 | 12/2015 | Spool et al. | |
| 2004/0238391 | A1 * | 12/2004 | Pond | A61C 19/02 206/369 |
| 2005/0256453 | A1 * | 11/2005 | Nagamatsu | A61M 25/1018 141/2 |
| 2010/0012537 | A1 * | 1/2010 | Farrar | B65D 77/046 206/364 |
| 2013/0062245 | A1 * | 3/2013 | Folchini | A61M 5/002 493/162 |
| 2016/0015457 | A1 | 1/2016 | Hurst | |
| 2016/0136352 | A1 * | 5/2016 | Smith | A61M 5/008 206/366 |
| 2018/0361056 | A1 * | 12/2018 | Horlock | A61M 5/002 |
| 2019/0038829 | A1 * | 2/2019 | Nasker | A61B 50/22 |
| 2020/0289741 | A1 * | 9/2020 | Pfrang | B65D 77/0446 |
| 2022/0008645 | A1 * | 1/2022 | Ukai | A61M 5/3129 |

FOREIGN PATENT DOCUMENTS

| | | | |
|---|---|---|---|
| EP | 0790063 | A1 | 8/1997 |
| EP | 3437678 | A1 | 2/2019 |
| RU | 19746 | U1 | 10/2001 |
| RU | 2329003 | C1 | 7/2008 |
| RU | 130837 | U1 | 8/2013 |
| RU | 2015129115 | A | 1/2017 |
| RU | 2695559 | C2 | 7/2019 |
| WO | 2018038077 | A1 | 3/2018 |

OTHER PUBLICATIONS

International Preliminary Report on Patentability for PCT/EP2021/065868 dated Dec. 29, 2022, 13 pages.

* cited by examiner

TRAY FOR RECEIVING A PLURALITY OF MEDICAL HOLLOW BODIES

CROSS REFERENCE TO RELATED APPLICATIONS

This application is a U.S. National Stage Application under 35 U.S.C. 371 of International Application No. PCT/EP2021/065868, filed Jun. 11, 2021, which claims priority to German Patent Application 10 2020 207 588.3, filed on Jun. 18, 2020. The contents of each of the which are hereby incorporated by reference in their entirety into the present disclosure.

The invention relates to a tray for holding a plurality of medical hollow bodies.

From the U.S. Pat. No. 6,216,885 B1 a tray for holding a plurality of syringes is known, which is made of a thermoformed plastic material and in particular is deep-drawn. This tray has a very low rigidity and is therefore difficult to handle. In order to be able to handle the tray, gripping spigots are provided at regular intervals, on which vacuum grippers, for example, can engage in order to hold the tray. The tray is designed for a specific syringe format, with fixed clamping elements to hold syringes of the specific format stably and securely. Thus, the tray cannot be used flexibly for different syringe formats, and because of the clamping elements holding the syringes stably in place, it is laborious to load the tray with the syringes or to remove the syringes from the tray.

Trays are also known in which medical hollow bodies are loosely inserted, which is particularly disadvantageous if the medical hollow bodies comprise glass or are made of glass. Glass-glass contact then occurs, which can lead to damage, particularly during transport. In particular, labels arranged on the medical hollow bodies may also be damaged or impaired with respect to their readability.

The invention is therefore based on the task of creating a tray for holding medical hollow bodies, in which the above-mentioned disadvantages are at least partially eliminated, while preferably not having the disadvantages.

The task is solved by providing the present technical teaching, in particular the teaching of the independent claims as well as the embodiments disclosed in the dependent claims and the description.

In particular, the task is solved by providing a tray for receiving a plurality of medical hollow bodies, comprising a bottom plate. The bottom plate has a top side and a bottom side. Along outer edges of the tray, an all-around wall is arranged on the top side. The bottom plate and the wall define a receiving volume for receiving the medical hollow bodies. The tray has a finite length along a longitudinal direction and a finite width along a width direction perpendicular to the longitudinal direction. The tray has at least one holding structure for holding medical hollow bodies. The holding structure, in turn, has a first holding wall extending from a first width portion of the wall to an opposite second width portion of the wall in a longitudinal direction. Spaced apart first breakthroughs are formed in the first holding wall. The holding structure further comprises a second holding wall spaced from the first holding wall by a first width distance and extending parallel to the first holding wall from the first width portion to the second width portion. Spaced apart second breakthroughs are formed in the second holding wall. Each of the second breakthroughs is aligned with a respective first breakthrough associated therewith. In particular, the second breakthroughs and the first breakthroughs are associated with each other in pairs, with the paired first and second breakthroughs being aligned with each other. The holding structure further comprises a row of distance elements spaced from the holding walls by a second width distance and extending parallel to the holding walls, the distance elements being spaced from each other to form a plurality of spaces. The distance elements are offset from the breakthroughs such that each of the spaces is aligned with a respective one of the first and second breakthroughs. Each pair of a first breakthrough and a second breakthrough is thus associated with a clearance space, the corresponding clearance space being aligned with the respective first breakthrough and with the respective second breakthrough of the correspondingly associated pair of first and second breakthroughs. A holding position for a medical hollow body is defined by a respective one of the spaces, the first breakthrough associated with that space, and the second breakthrough associated with the space and the first breakthrough, the holding position extending in the width direction of the tray. The first width distance is smaller than the second width distance.

Due to the geometric structure with the bottom plate and the all-round circumferential wall, which together delimit the receiving volume, the tray has a high degree of rigidity and can thus be handled easily and stably at the same time. In particular, there is no need for special gripping sockets, so that the volume that would otherwise have to be provided can be saved and used to hold medical hollow bodies. With the holding positions formed by the openings and spaces, the holding structure is very flexible and can be used with a variety of different formats of medical hollow bodies, in particular a variety of syringe formats—regardless of whether a finger rest, piston rod and/or injection needle is/are already mounted. At the same time, the holding structure dispenses with fixed clamping elements, so that the medical hollow bodies can be inserted into and removed from the tray easily and quickly, in particular manually or also mechanically—in particular by means of a robot. The tray thus enables easy loading with medical hollow bodies and also easy removal of the same. At the same time, the holding positions provide a clear insertion pattern for further processing of the medical hollow bodies. Furthermore, the holding positions define clear, spaced-apart areas for the individual medical hollow bodies, so that glass-to-glass contact in particular is avoided. This also eliminates the risk of damage to the medical hollow bodies and/or the labels that may be arranged thereon. In particular, their readability is not impaired when using the tray proposed herein.

In particular, with the tray proposed herein, an exact number of inserted medical hollow bodies can be correctly tracked. A plurality of different formats and variations of medical hollow bodies can be covered by a single tray. In particular, different syringe formats with and without piston rods and/or finger rests can be separated when using the tray proposed herein. Due to the precise fit provided by means of the holding positions, slipping of the medical hollow bodies during transport is excluded.

The bottom plate is preferably flat and level. In particular, the bottom plate is free of protuberances and/or protrusions.

In particular, the tray is not deep-drawn.

Preferably, the tray is manufactured by injection molding. In particular, due to the robustness of the injection-molded material, the tray can be used multiple times, in particular more often than thermoformed material. In particular, the tray can be used as a circulation material.

Due to the arrangement of the retaining walls on the one hand and the distance elements forming the spaces on the other hand, incorrect insertion of the medical hollow bodies is excluded.

Preferably, the wall extends at 90° to the bottom plate. In particular, the wall extends in a vertical direction starting from the bottom plate. The vertical direction is perpendicular on the one hand to the longitudinal direction and on the other hand to the width direction.

The longitudinal direction is preferably a direction of longest extension of the tray. The width direction preferably corresponds to a direction in which the tray extends over a width that is shorter than the length over which the tray extends along the longitudinal direction. In particular, the vertical direction is a direction in which the tray extends in a vertical direction when the tray is arranged as intended, i.e., in a geodetic vertical direction. In contrast, the longitudinal direction and the width direction extend in a plane to which the vertical direction, the vertical in space when the tray is arranged as intended, is perpendicular.

Preferably, the wall extends in the upward direction to at least an upper edge of a largest medical hollow body insertable into the receiving volume when inserted into the receiving volume. Preferably, the wall extends to above the top edge of the largest hollow medical body to be placed in the receiving volume when the hollow medical body is placed in the receiving volume.

Preferably, the retaining walls are as high in the upward direction as the wall, thus extending in particular from the bottom plate in the upward direction to an upper edge of the wall.

The perforations are preferably open in the upward direction, thus having an open end facing away from the bottom plate.

The tray is particularly usable with the following tip formats: 1 ml, diameter 8.15 mm, both with and without piston rod/finger rest, the glass body length being 81.2 mm with Vetter RNS (Rigid Needle Shield) and 73.9 mm with Vetter OVS; 1.5 ml, diameter 10.85 mm, both with and without piston rod/finger rest, with a glass body length with RNS of 73.3 mm and with Vetter OVS of 63.5 mm; 2.25 mm, diameter 10.85 mm, both with and without piston rod/finger rest, with a glass body length with Vetter RNS of 82.8 mm and with Vetter OVS of 75 mm. Vetter OVS, Vetter TipCap, Vetter NS (Needle Shield) and Vetter RNS can be used as closure parts.

The length of the tray measured in the longitudinal direction is preferably from at least 300 mm to at most 400 mm, preferably from at least 325 mm to at most 375 mm, preferably 350 mm.

The width of the tray measured in the width direction is preferably from at least 200 mm to at most 300 mm, preferably from at least 225 mm to at most 295 mm, preferably from at least 250 mm to at most 280 mm, preferably from at least 265 mm to at most 275 mm, preferably 270 mm.

The tray is preferably designed as a tray insert for insertion or insertion into a larger transport tray, wherein a plurality of such trays can be inserted or inserted into the transport tray. The dimensions of the tray, in particular its length and its width, are preferably such that two such trays can be inserted side by side into the transport tub. The height of the tray is in particular dimensioned such that a plurality of trays, in particular more than two trays, preferably four or more trays, can be inserted one above the other into such a transport tray.

A height of the tray measured in the vertical direction is from a lower edge of the bottom plate to an upper edge of the wall of at least 15 mm to at most 30 mm, preferably from at least 17.5 mm to at most 25 mm, preferably from at least 20 mm to at most 23 mm, preferably 22 mm. If the tray additionally has foot elements, its height including the foot elements is preferably from at least 23 mm to at most 30 mm, preferably from at least 24 mm to at most 28 mm, preferably 26 mm.

The first width distance is preferably from at least 6 mm to at most 12 mm, preferably 9 mm. The second width distance is preferably from at least 26 mm to at most 30 mm, preferably 28 mm. The third width distance is preferably from at least 36 mm to at most 42 mm, preferably 39 mm. A single clearance of the spaces preferably has an extension, i.e. clear width, measured in the longitudinal direction of the tray of from at least 6 mm to at most 12 mm, preferably 9 mm. Preferably, all spaces are identically formed.

According to a further development of the invention, it is provided that the tray has, as the at least one holding structure, two holding structures which are arranged next to one another in the width direction and are separated from one another by a separating wall extending in the longitudinal direction from the first width portion to the second width portion. The tray thus has a total of two holding structures, and in particular two holding positions in each case are also arranged next to one another in the width direction. The tray can thus accommodate two rows of medical hollow bodies side by side in the width direction, which means that the hollow bodies of the two rows are each arranged in pairs one behind the other in the tray, as viewed in the longitudinal direction of the hollow bodies. In this way, the tray can very functionally accommodate a plurality of medical hollow bodies in an orderly manner.

The separating wall preferably extends in the vertical direction up to the upper edge of the wall, i.e. is formed as high as the wall.

According to a further development of the invention, it is provided that the first holding wall of the at least one holding structure is spaced from a end wall, which is selected from a longitudinal portion of the wall and the separating wall, by a third width distance. Preferably, this applies to both holding structures of the tray when the tray has two holding structures. In this case, for one holding structure of the two holding structures, the end wall is the longitudinal portion of the wall; for the other holding structure of the two holding structures, the end wall is the separating wall separating the two holding structures. Advantageously, a piston rod of a medical hollow body may be accommodated in a region arranged between the first holding wall and the end wall, if the medical hollow body comprises such a piston rod.

According to a further development of the invention, it is provided that the width portions of the wall each comprise a recess between the second holding wall and the row of distance elements. This recess advantageously permits simple engagement with a gripper or also manually with the hand, for example with a finger, in order in particular to be able to insert medical hollow bodies, which are arranged at the edge, safely and easily into the tray and remove them again.

The recesses are preferably open at the top, i.e. have an open end facing away from the bottom plate.

According to a further development of the invention, it is provided that the bottom plate has an elevation in the region of the row of distance elements. In particular, the bottom plate may have a shape deviating from the plane in the region of the distance elements and, in particular, an upward bulge. The distance elements are arranged on the elevation. In the region of the spaces, the elevation provides a support area for the medical hollow bodies which is offset from a remaining bottom surface of the tray, so that the hollow bodies do not rest on the bottom surface, in particular in the region between the second holding wall and the row of distance elements. The hollow bodies can then be easily grasped, in particular gripped there. The elevation also leads structurally to a stiffening of the tray, so that it has a particularly high stability. On the bottom side of the bottom plate, the elevation on the top side forms a recess which in turn makes it particularly easy to grip and handle the tray itself, either manually or mechanically. In particular, the elevation formed on the top side forms an engagement groove on the bottom side, with which in particular easy removal of the tray from a transport tray is possible.

According to a further development of the invention, it is provided that the distance elements are elongated when viewed in top view. This represents a particularly simple and easy-to-manufacture design of the distance elements.

Alternatively, it is preferably provided that the distance elements are cross-shaped when viewed in top view. The distance elements thus fulfill an additional function in addition to spacing the medical hollow bodies, in that they contribute to the stiffening and thus the stability of the tray due to their cross-shaped structure. In particular, due to this structural reinforcement, a high stacking of a plurality of trays on top of each other is possible.

According to a further embodiment of the invention, it is provided that the bottom plate has foot elements on its bottom side. In a preferred embodiment, the tray may have four foot elements on the bottom side of the bottom plate, in particular one foot element at each corner. The foot elements protrude from the bottom side—geodetically downwards. They thus form stand-up elements on which the tray can stand up, the bottom side of the bottom plate then being spaced from a stand-up plane on which the tray stands up. Preferably, the foot elements are offset inwardly from the outer edges of the bottom plate by at least one wall thickness of the wall. Particularly preferably, they are arranged offset inwardly by exactly the wall thickness of the wall. In particular, this permits stable stacking of a plurality of trays one on top of the other, with the foot elements of an upper tray in each case engaging in the receiving volume of the lower tray and thereby preferably resting stably against the wall on the inside. This fit of the foot elements, which is in particular a tight fit, preferably effectively prevents the stacked trays from slipping relative to one another.

According to a further development of the invention, it is provided that the tray is formed in one piece and of uniform material, the tray can be produced in this way in a particularly simple and inexpensive manner, in particular by injection molding.

The tray is preferably formed in one piece and of uniform material, preferably from a plastic. The tray can be produced in this way in a particularly simple and cost-effective manner, in particular by injection molding. The plastic is preferably selected from a group consisting of: An autoclavable plastic, a machine-rinseable plastic, acrylonitrile-butadiene-styrene-copolymer (ABS), polycarbonate, and polypropylene. In particular, these plastics allow easy cleaning of the tray, especially using a dishwasher, and the tray is preferably also autoclavable. In particular, this allows the tray to be reused, especially to be used in a recirculating process.

The invention also includes the tray according to the invention or a tray according to one of the previously described embodiments in combination with a medical hollow body, in particular one of the medical hollow bodies described above, with which the tray can preferably be used. The medical hollow body includes a cylinder portion and a flange area. When the medical hollow body is disposed in the tray, the flange area is disposed between the first holding wall the second holding wall. In this regard, the flange area preferably engages behind a second breakthrough of the second breakthroughs associated with the medical hollow bodies. The cylinder portion extends in the width direction of the tray through the second breakthroughs and into the spaces associated with that second breakthrough associated with the medical hollow bodies. In this way, the medical hollow bodies is securely and stably held in the tray. In particular, it cannot slip in the tray and cannot come into contact with other medical hollow bodies received in the tray. In this way, in particular, glass-glass contact between the medical hollow bodies arranged in the tray is avoided.

The flange of the medical hollow bodies can be, in particular, a finger rest or a backstop. The medical hollow body is arranged with clearance—in particular depending on its outer diameter—at least in the spaces, optionally also at least in the second breakthroughs. The dimensions of the tray are thereby preferably adapted to a largest medical hollow body to be arranged in the tray in such a way that this can just be arranged at the holding position without fixed clamping, preferably with little space. If the medical hollow body is designed as a syringe, an injection end of the syringe is preferably arranged between the row of distance elements and a rear end wall, the rear end wall in turn being selected from a longitudinal portion of the wall and the separating wall, depending on which holding structure the row of distance elements is assigned to. The separating wall is thus in particular the rear end wall for a first holding structure of the two holding structures, and the front end wall for a second holding structure of the two holding structures.

According to a further development of the invention, it is provided that a piston rod of the medical hollow bodies extends through the first breakthroughs in the direction of the end wall. Thus, the third width distance is available in particular for arranging the piston rod.

Figure 2:
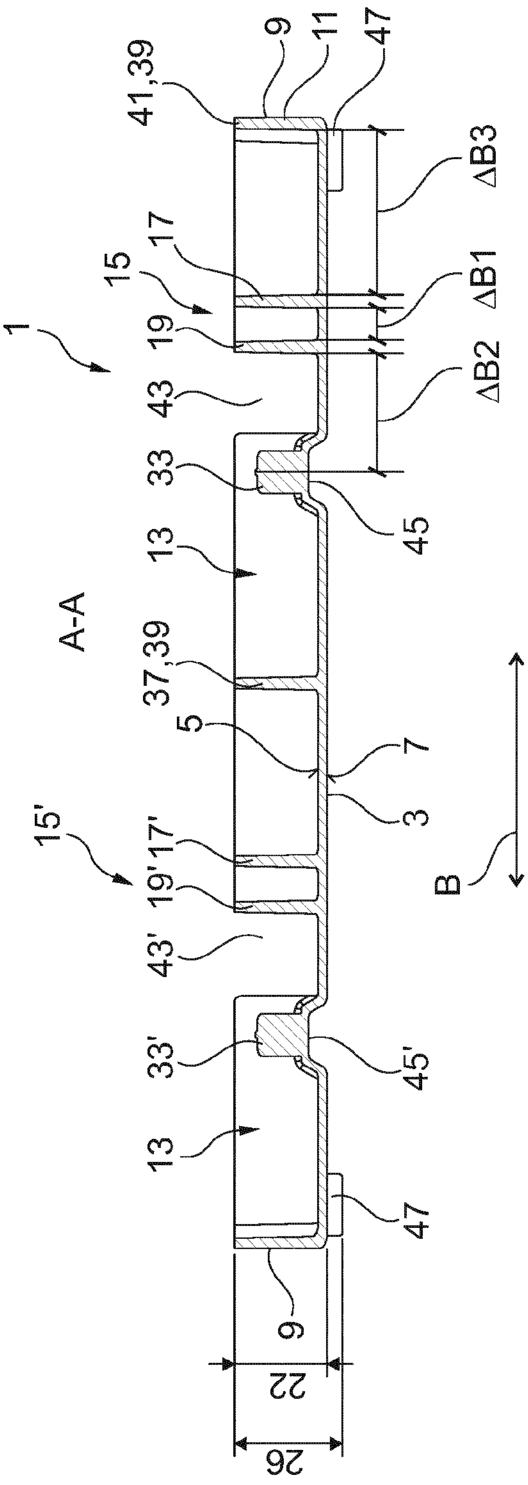
Figure 3:
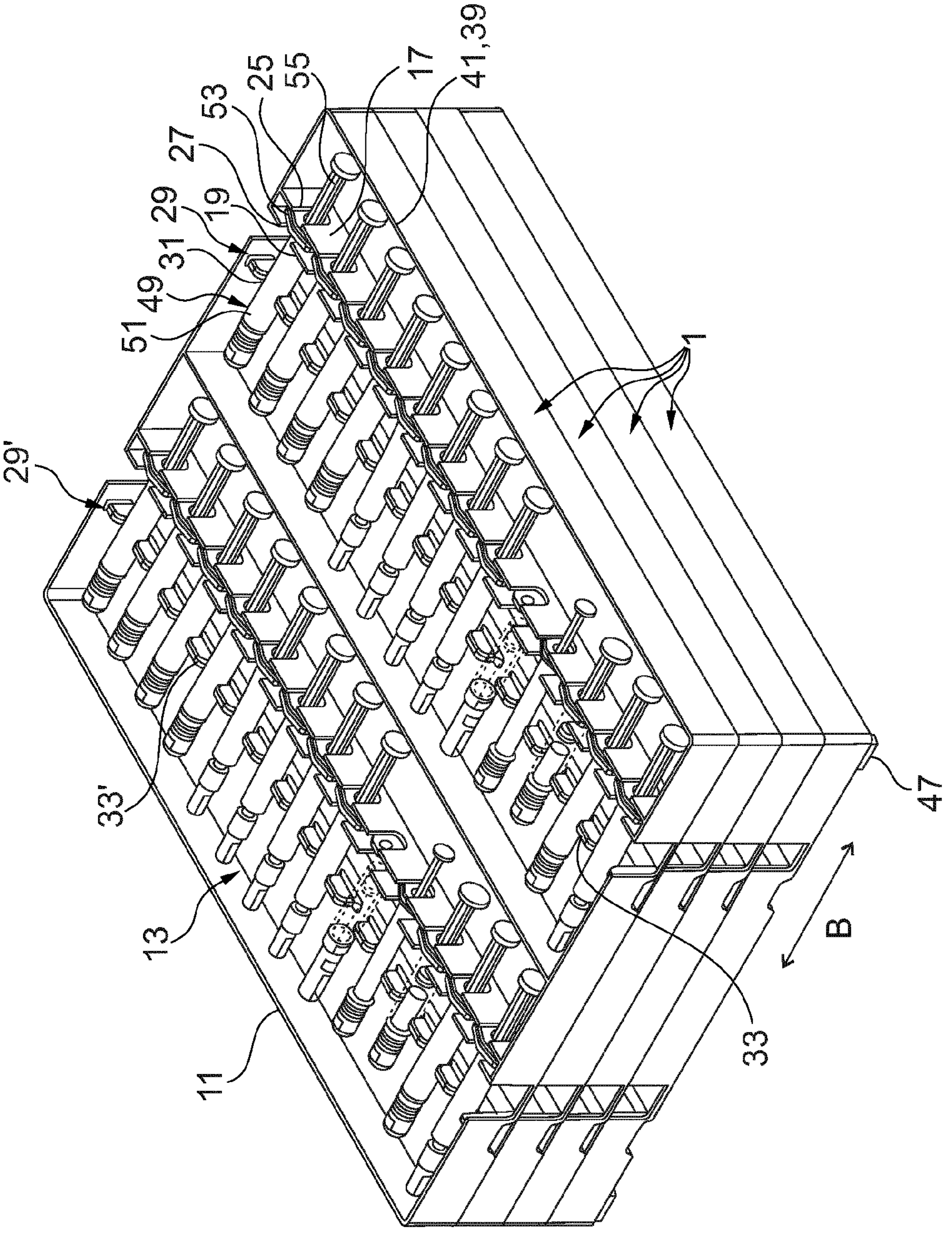

The invention is explained in more detail below with reference to the drawing. Thereby show:

FIG. 1 a first embodiment of a tray;

FIG. 2 a cross-sectional view of the first embodiment of the tray along the line A-A shown in FIG. 1, and FIG. 3 a representation of a plurality of stacked trays according to a second embodiment in combination with medical hollow bodies.

FIG. 1 shows an illustration of a first embodiment of a tray 1 adapted to receive a plurality of medical hollow bodies. The tray 1 comprises a bottom plate 3 having a top side 5 and a bottom side 7. Along outer edges 9 of the tray 1, an all-around wall 11 is disposed on the top side 5. The bottom plate 3 and the wall 11 define a receiving volume 13 for receiving the medical hollow bodies. The tray 1 has a finite length along a longitudinal direction L and a finite width along a width direction B perpendicular to the longitudinal direction L. The tray 1 further comprises a holding structure 15 for holding medical hollow bodies.

In particular, the tray 1 here comprises a first holding structure 15 and a second holding structure 15'. The two holding structures 15, 15' are of identical design, so that in this respect only the design of the first holding structure 15 will be discussed in more detail below. The corresponding elements of the second holding structure 15' are each shown with apostrophed reference signs.

The holding structure 15 has a first holding wall 17 which extends in longitudinal direction L from a first width portion 21 of the wall 11 to an opposite second width portion 23 of the wall 11. In this regard, first breakthroughs 25 are formed in the first holding wall 17 and are spaced apart from each other. The holding structure 17 further comprises a second holding wall 19 spaced from the first holding wall 17 by a first width distance B1. The second holding wall 19 thereby extends parallel to the first holding wall 17 from the first width portion 21 to the second width portion 23. Second breakthroughs 27 are formed in the second holding wall 19, which are spaced apart from each other. In this regard, each of the second breakthroughs 27 is aligned with a respective first breakthrough 25 associated therewith. The holding structure 15 further comprises a row 29 of distance elements 33 spaced from the holding walls 17, 19 by a second width distance B2, the row 29 extending parallel to the holding walls 17, 19, and the distance elements 33 being spaced from each other to form a plurality of spaces 31. The distance elements 33 are arranged offset from the breakthroughs 25, 27 such that each of the spaces 31 is aligned with a respective one of the first breakthroughs 25 and the second breakthroughs 27. In this manner, a holding position 35 for a medical hollow body is defined by each of the spaces 31, the first breakthroughs 25 associated therewith, and the second breakthroughs 27 associated therewith, the holding position 35 extending in the width direction B.

The first width distance B1 is smaller than the second width distance B2.

The first holding structure 15 and the second holding structure 15' are arranged adjacent to each other in the width direction B and separated from each other by a separating wall 37 extending in the longitudinal direction L from the first width portion 21 to the second width portion 23.

The first holding wall 17 is spaced from a end wall 39 by a third width distance B3. In this case, the end wall 39 is a longitudinal portion 41 of the wall 11. The first holding wall 17' of the second holding structure 15' is also spaced from a further end wall 39' by the third width distance B3. In this case, the further end wall 39' is the separating wall 37.

The width portions 21, 23 of the wall 11 each have a recess 43 between the second holding wall 19 and the row 29 of distance elements 33.

The bottom plate 3 has an elevation 45 in the region of the row 29 of distance elements 33. The distance elements 33 are arranged on the elevation 45.

In the first embodiment shown in FIG. 1, the distance elements 33 are cross-shaped in top view.

The bottom plate 3 has foot elements 47 on its bottom side 7, which protrude from the bottom side 7. In this connection, the foot elements 47 are preferably offset inwardly from the outer edges 9 of the bottom plate 3 by at least one wall thickness of the wall 11, preferably by the wall thickness.

The tray 1 is in particular formed in one piece and of uniform material, preferably of a plastic. The plastic is preferably selected from a group consisting of: An autoclavable plastic, a machine rinsable plastic, acrylonitrile-butadiene-styrene-copolymer, polycarbonate, and polypropylene.

FIG. 2 shows a cross-sectional view of the tray 1 according to the first embodiment along the line A-A shown in FIG. 1. In particular, the first width distance B1, the second width distance B2 under third width distance B3 are drawn in FIG. 2. In addition, it is drawn in FIG. 2 that the height of the tray 1 measured in the upward direction including the foot elements 47 is 26 mm, the height minus the foot elements 47 being 22 mm.

FIG. 3 shows a representation of a plurality of trays 1 stacked one on top of the other according to a second embodiment example in combination with a plurality of medical hollow bodies 49. Identical and functionally identical elements are provided with the same reference signs, so that in this respect reference is made to the preceding description. However, for clarity of presentation, only one of the hollow bodies 49 is designated with the corresponding reference sign and also with further reference signs relating to the hollow body 49.

In particular, the foot elements 47 enable the plurality of trays 1 to be stacked stably one on top of the other without the risk of the individual trays 1 slipping relative to one another. For this purpose, in particular the foot elements 47 of the respective upper trays 1 engage in the receiving volumes 13 of the respective lower trays 1 and preferably rest on the inside against the respective walls 11. In this second embodiment example of the tray 1, the distance elements 33, 33' are elongated when viewed in top view.

The medical hollow bodies 49 are formed here in particular as syringes. In the following, only one of the medical hollow bodies 49 will be described in more detail. The medical hollow bodies 49 are preferably identical or at least similarly configured in this respect. The medical hollow body 49 considered in more detail here has a cylinder portion 51 and a flange area 53, the flange area 53 being arranged between the first holding wall 17 and the second holding wall 19. In doing so, it engages behind a second breakthrough 27 associated with the medical hollow body 49. The cylinder portion 51 extends in the width direction B of the tray 1 through the second breakthrough 27 and into the spaces 31 associated with the second breakthrough 27, which in turn is associated with the medical hollow body 49.

A piston rod 55 of the medical hollow bodies 49 extends through the first breakthroughs 25 toward the end wall 39.

The flange area 53 is preferably formed as a finger rest or a backstop.

Deviating from the representation selected here, however, medical hollow bodies 49 can also be accommodated in the tray 1 which are not yet assembled, i.e. in particular do not yet have a flange area 53 and/or a piston rod 55.

The invention claimed is:

1. A tray (1) for holding a plurality of medical hollow bodies (49), comprising a bottom plate (3) having a top side (5) and a bottom side (7), wherein an all-around wall (11) is disposed along outer edges (9) of the tray (1) on the top side (5), wherein the bottom plate (3) and the wall (11) delimit a receiving volume (13) for receiving the medical hollow bodies (49), wherein the tray (1) has a finite length along a longitudinal direction (L) and a finite width along a width direction (B) perpendicular to the longitudinal direction (L), wherein the tray (1) comprises at least one holding structure (15) for holding medical hollow bodies (49), wherein the at least one holding structure (15) is devoid of a fixed clamping element, wherein the at least one holding structure (15) comprises:

a first holding wall (17) extending from a first width portion (21) of the wall (11) to an opposite second width portion (23) of the wall (11) in the longitudinal direction (L), spaced first breakthroughs (25) being formed in the first holding wall (17), a second holding wall (19) spaced from said first holding wall (17) by a first width distance (ΔB1) and extending parallel to said first holding wall (17) from said first width portion (21) to said second width portion (23), said second holding wall (19) having formed therein spaced second breakthroughs (27), each of said second breakthroughs (27) being aligned with an associated one of said first breakthroughs (25), and a row (29) of distance elements (33) spaced from the first holding wall and the second holding wall (17, 19) by a second width distance (ΔB2) and extending parallel to the first holding wall and the second holding wall (17,19) to form a plurality of spaces (31), the distance elements (33) being arranged offset from the first breakthroughs (25,27) such that each of the spaces (31) is aligned with a respective one of the first and second breakthroughs (25,27) so that a clamp-free holding position (35) for a medical hollow body (49) is defined by a respective one of said spaces (31), an associated first breakthrough (25) and an associated second breakthrough (27), said holding position (35) extending in width direction (B), and wherein the first width distance (ΔB1) is smaller than the second width distance (ΔB2).

2. The tray (1) according to claim 1, wherein the tray (1) comprises as the at least one holding structure (15) two holding structures (15,15') arranged side by side in width direction (B) and separated from each other by a separating wall (37) extending in longitudinal direction (L) from the first width portion (21) to the second width portion (23).

3. The tray (1) according to claim 1, wherein the first holding wall (17) of the at least one holding structure (15) is spaced from a end wall (39) selected from a longitudinal portion (41) of the all-around wall (11) and the separating wall (37) by a third width distance (ΔB3).

4. The tray (1) according to claim 1, wherein the width portions (21,23) of the all-around wall (11) each comprise a recess (43) between the second holding wall (19) and the row (29) of distance elements (33).

5. The tray (1) according to claim 1, wherein the bottom plate (3) has an elevation (45) in the region of the row (29) of distance elements (33), wherein the distance elements (33) are arranged on the elevation (45).

6. The tray (1) according to claim 1, wherein the distance elements (33) are elongated or cross-shaped in top view.

7. The tray (1) according to claim 1, wherein the bottom plate (3) has foot elements (47) on the bottom side (7), which protrude from the bottom side (7).

8. The tray (1) according to claim 1, wherein the tray (1) is formed in one piece and of uniform material.

9. The tray (1) according to claim 1 in combination with a medical hollow body (49), wherein the medical hollow body (49) comprises a cylinder portion (51) and a flange area (53), wherein the flange area (53) is arranged between the first holding wall (17) and the second holding wall (19), wherein the cylinder portion (51) extends in width direction (B) of the tray (1) through the second breakthrough (27) and into the spaces (31) associated with the second breakthrough (27) associated with the medical hollow bodies (49).

10. The tray (1) according to claim 9 in combination with the medical hollow bodies (49), wherein a piston rod (55) of the medical hollow bodies (49) extends through the first breakthrough (25) towards the end wall (39).

* * * * *